United States Patent
Dintakurty et al.

(10) Patent No.: US 11,386,704 B2
(45) Date of Patent: Jul. 12, 2022

(54) CLINICAL INTEGRATION OF FACIAL RECOGNITION PROCESSING

(71) Applicant: CERNER INNOVATION, INC., Kansas City, KS (US)

(72) Inventors: Lakshmi Prasad Dintakurty, Downingtown, PA (US); Lin-Hung Wu, Kennett Square, PA (US); Jedd Anthony L. Cuison, Malvern, PA (US); Jeffrey Ismail Mahmood, Trappe, PA (US); Julia Ann Vu, Landisville, PA (US)

(73) Assignee: CERNER INNOVATION, INC., North Kansas City, MO (US)

( * ) Notice: Subject to any disclaimer, the term of this patent is extended or adjusted under 35 U.S.C. 154(b) by 19 days.

(21) Appl. No.: 16/531,192

(22) Filed: Aug. 5, 2019

(65) Prior Publication Data

US 2021/0042505 A1 Feb. 11, 2021

(51) Int. Cl.
*G06V 40/16* (2022.01)
*G16H 40/20* (2018.01)
*G16H 10/60* (2018.01)

(52) U.S. Cl.
CPC ........... *G06V 40/172* (2022.01); *G16H 10/60* (2018.01); *G16H 40/20* (2018.01)

(58) Field of Classification Search
CPC .... G06K 9/00288; G16H 10/60; G16H 40/20; G16H 40/67; G16H 50/20; G16H 50/30; G06V 40/172
See application file for complete search history.

(56) References Cited

U.S. PATENT DOCUMENTS

| | | | | |
|---|---|---|---|---|
| 9,704,026 | B1* | 7/2017 | Appelman | 382/118 |
| 10,078,728 | B2* | 9/2018 | Raduchel | G16H 10/60 705/2 |
| 10,140,504 | B2* | 11/2018 | Finkelstein | H04W 12/06 382/118 |
| 2009/0136094 | A1* | 5/2009 | Driver | G16H 10/60 382/115 |
| 2012/0116800 | A1* | 5/2012 | McCallie | G06Q 10/10 705/2 |
| 2015/0087257 | A1* | 3/2015 | Balram | H04W 4/12 455/404.1 |
| 2018/0068173 | A1* | 3/2018 | Kolleri | G06K 9/00268 382/118 |
| 2019/0159009 | A1* | 5/2019 | Barash | H04W 4/90 370/310 |

* cited by examiner

*Primary Examiner* — Emily C Terrell
*Assistant Examiner* — Molly Delaney
(74) *Attorney, Agent, or Firm* — Shook Hardy & Bacon L.L.P.

(57) ABSTRACT

Embodiments herein disclose systems, methods, and computer-readable media for integrating facial recognition technology into clinical workflows. An application can manage receipt of a source image, including a face of an unidentified individual, and communicate the source image for facial recognition processing. The facial recognition processing can identify an individual and demographic information associated thereto, as well as provide information to access an electronic health record server housing one or more electronic health records. The application can access health-related data for the individual from the individual's EHR and rank the accessed information to communicate to a source device in a custom, prioritized communication.

18 Claims, 5 Drawing Sheets

CLINICAL INTEGRATION OF FACIAL RECOGNITION PROCESSING

BACKGROUND

Each year, many unconscious and unidentified individuals are admitted to the emergency department ("ED"). While first responders and clinicians are trained to react without an identification, the care provided certainly benefits from accurate health data regarding the patient. Treatment to unidentified individuals is currently provided without any diagnoses, allergies, or health data.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description and Drawings.

In brief and at a high level, embodiments of the present invention provide systems, methods, and computer-readable media for clinical integration of facial recognition capabilities. Embodiments provide an application that coordinates with various components of a system to integrate facial recognition analysis into clinical workflows.

One embodiment provides one or more non-transitory computer-readable media having computer-executable instructions embodied thereon that, when executed by a processor of a computer device, perform a method. The method comprises receiving an image of an individual from a source device, wherein the image comprises a face of the individual; receiving a unique identifier associated with the face of the individual; utilizing the unique identifier, accessing demographic information of the individual, wherein the demographic information is derived from an electronic health record of the individual; communicating the demographic information to the source device; accessing one or more of at least one problem associated with the individual or at least one allergy associated with the individual; and communicating the at least one problem or the at least one allergy to the source device.

Another embodiment provides one or more non-transitory computer-readable media having computer-executable instructions embodied thereon that, when executed by a processor of a computer device, perform a method. In accordance with the media, the method comprises receiving an image of an individual from a source device, wherein the image comprises a face of the individual; receiving a unique identifier associated with the face of the individual; utilizing the unique identifier, accessing demographic information of the individual, wherein the demographic information is derived from an electronic health record of the individual; communicating the demographic information to the source device; accessing one or more of at least one problem associated with the individual or at least one allergy associated with the individual; communicating the at least one problem or the at least one allergy to the source device; and generating a pre-arrival note for the individual prior to arriving at a destination, wherein the pre-arrival note is pre-populated with at least the demographic information.

Yet another embodiment provides a system for clinical integration of facial recognition. The system comprises one or more processors configured to: receive an image of an individual from a source device, wherein the image comprises a face of the individual; receive a unique identifier associated with the face of the individual; utilize the unique identifier to access demographic information of the individual, wherein the demographic information is derived from an electronic health record of the individual; communicate the demographic information to the source device; query the electronic health record to determine if one or more of at least one problem or at least one allergy is associated with the individual; and communicate at least one of (i) a notification indicating there is not at least one problem or at least one allergy associated with the individual in the electronic health record, (ii) the at least one problem, or (iii) the at least one allergy to the source device.

BRIEF DESCRIPTION OF THE DRAWINGS

Embodiments are described in detail below with reference to the attached drawings figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-useable instructions embodied on one or more computer-readable media, as discussed further herein.

Embodiments of the present invention provide systems, methods, and computer-readable media for clinical integration of facial recognition capabilities. At a high level, embodiments of the present invention provide a customized and complex software product that specifically addresses a need to integrate facial recognition technology with electronic health record (EHR) technology. The software product can communicate with one or more disparate sources to, among other things, provide health data from an EHR, store health data in an EHR, generate one or more health documentation forms (e.g., a pre-arrival visit form), and the like. The software product can provide the integration with an EHR system while preserving privacy of an individual and the data associated therewith accessed from the EHR system.

Figure 1:
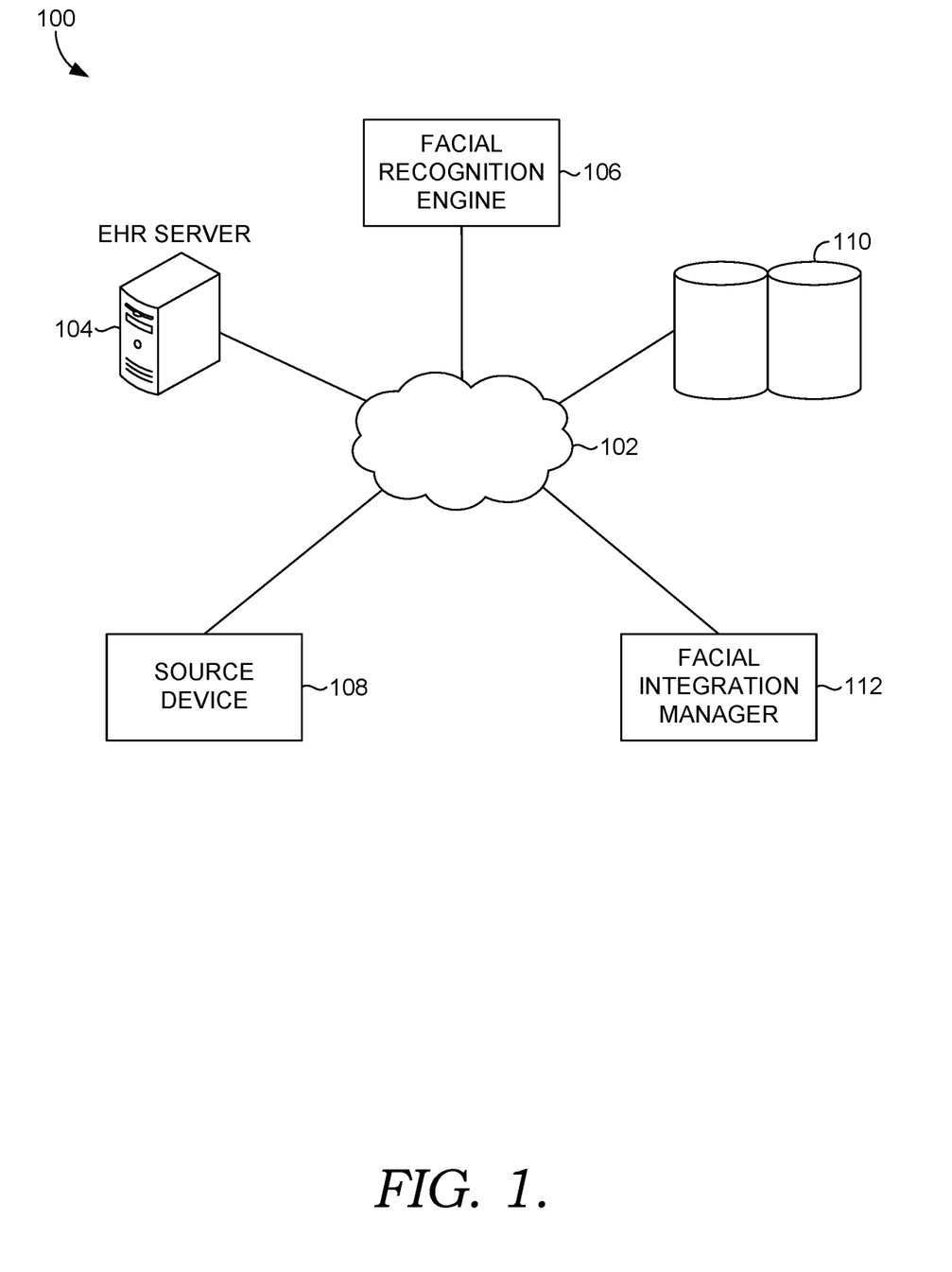
FIG. 1 depicts a block diagram of an exemplary system architecture in accordance with an embodiment of the present invention.

Referring to the drawings in general, an initially to FIG. 1, a block diagram illustrating an exemplary system 100 architecture in which some embodiments of the present disclosure may be employed. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

It should be understood that the system 100 shown in FIG. 1 is an example of one suitable computing system architecture. Each of the components of FIG. 1 may be implemented via any type of computing device. The components can communicate with each other via a network including, without limitation, one or more local area networks (LANs) and/or wide area networks (WANs). Such networking environments are commonplace in offices, enterprise-wide computer networks, intranets, and the Internet. It should be understood that any number of components shown in FIG. 1 may be employed within the system 100 within the scope of the present invention. Each may be implemented via a single device or multiple devices cooperating in a distributed environment. Additionally, other components not shown may also be included within the environment.

Among other components not shown, the system 100 includes a variety of user devices, such as source device 108, an EHR server 104, a facial recognition engine 106, a facial integration manager, and a database 110, any of which can interact with any other component of the system 100 and each of which are communicatively coupled with each other. These components may communicate with each other via networking means (e.g., network 102) which may include, without limitation, one or more local area networks LANs and/or wide area networks (WANs). In exemplary implementations, such networks comprise the Internet and/or cellular networks, amongst any of a variety of possible public and/or private networks.

Source device 108 can comprise any type of computing device capable of use by a user. By way of example and not limitation, a source device can be embodied as a personal computer (PC), a laptop computer, a mobile device, a smartphone, a tablet computer, a smart watch, a wearable computer, a fitness tracker, a personal digital assistant (PDA) device, a global positioning system (GPS) device, a video player, a handheld communications device, an embedded system controller, a camera, a remote control, a wearable electronic device with a camera (e.g., smart glasses, gesture-based wearable computers, etc.) a consumer electronic device, a workstation, or any combination of these delineated devices, a combination of these devices, or any other suitable computer device.

EHR server 104 maintains, and provides access to, one or more EHR database(s) containing records of treatment events, medication history, diagnoses, problems, allergies, substance use history, demographic attributes, history of violence, laboratory tests, time and date data, and any other health-related data, or any combination thereof for a plurality of patients. Additionally, the EHR database (such as data store 110) can include clinical notes, appointment notes, records of issued prescriptions, diagnoses, care plans, bloodwork, urinalysis, treatment data, emergency contact information, and the like, for each patient of a healthcare facility or a plurality of healthcare facilities. Further, EHR database can include images, representations, or clinical documentation of physical health data (e.g., burns, abrasions, scars, etc.). Additionally, in some embodiments, EHR server 104 can maintain one or more pharmaceutical formularies that identify prescriptions prescribed by, or available for prescription by, care providers.

Facial recognition engine 106 comprises instructions to perform facial recognition processing. In particular, and as described further herein, the facial recognition engine 106 can receive a source image, perform facial recognition processing, and compare to a reference image to determine if a face in the source image matches a face in the reference image. As used herein, a "reference image" refers to an image that is associated with a known individual (e.g., an image that has already undergone facial recognition processing and the results thereof are associated with a known individual) while a "source image" refers to an image that is communicated to undergo facial recognition software to identify an individual (i.e., an image that is not associated with a known individual). Any facial recognition software that can process a source image to identify facial coordinates and identify any matching reference images (or a lack thereof) can be utilized as the facial recognition engine 106, such as the Amazon Rekognition® facial recognition program.

Facial integration manager 112 can facilitate communication between a source device, such as source device 108, and a plurality of other sources such as an EHR system (such as EHR server 104), a data store (such as data store 110), facial recognition software (such as facial recognition engine 106), and the like. Facial integration manager 112 can include an application programming interface (API) library that includes specifications for routines, data structures, object classes, and variables that support the interaction of the facial integration manager 112 architecture and the software framework of one or more disparate sources (e.g., EHR server 104). These APIs can include configuration specifications for the system 100 such that the components therein may communicate with each other, as described herein.

Data store 110 can store a variety of data. While shown as a single database in FIG. 1, data store 110 can be multiple data stores and can be associated with different entities. For the sake of simplicity, data store 110 is described herein as a singular database that is in communication with multiple entities. One of skill in the art will understand the data store 110 can take a variety of forms, be represented as multiple components, and communicate with any number of sources. Data store 110 can include, among other things, health-related data for individuals such as EHRs, facial recognition data (discussed further herein) such as face identifiers and/or facial coordinates, patient identifiers, demographic information, public service URLs (discussed further herein), and the like.

Figure 2:
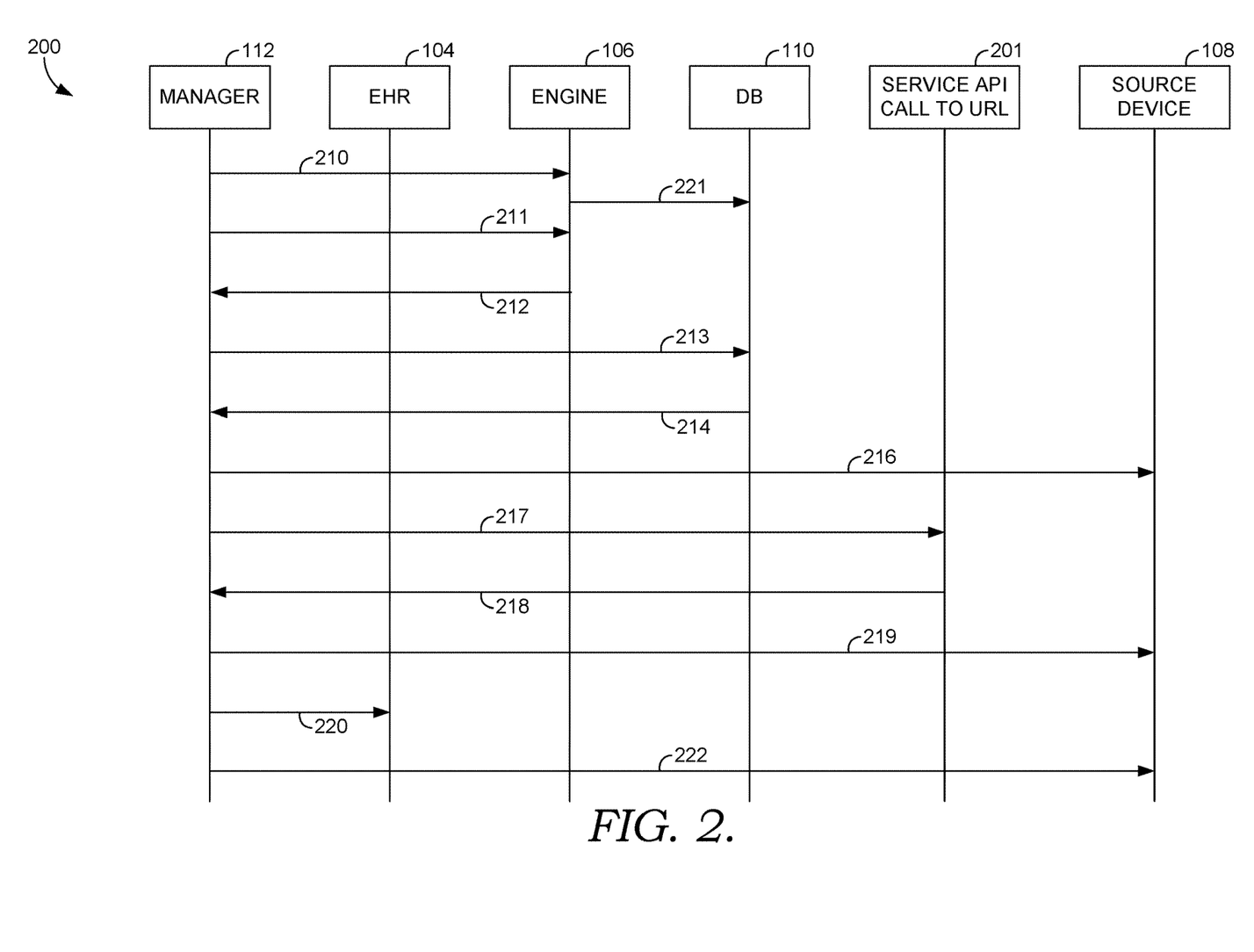
FIG. 2 depicts a diagram of exemplary component interactions in accordance with an embodiment of the present invention.

Having briefly described the components of system 100, exemplary component interactions of the components of FIG. 1 are now described with reference to FIG. 2. In application, a reference image is acquired. In embodiments, a reference image is acquired at a patient registration encounter at a healthcare facility, During said encounter, a patient may register and consent to analysis of a photo, with facial recognition data associated therewith, to be stored in a data store (such as data store 110). The reference image can be associated with a patient's name and date of birth as well as any other demographic information desired by the registration entity (e.g., sex, emergency contact(s), primary language, etc.). Once acquired, the registration entity can communicate the reference photo either directly to the facial recognition engine 106 or to the facial recognition engine 106 via the facial integration manager 112, as shown at instance 210 of FIG. 2. Reference images can be acquired from a plurality of sources including, but not limited to, healthcare facilities (e.g., hospitals, clinics, in-patient facilities, etc.), electronic health portals, insurance portals, social media networks, health data exchange platforms, national self-registrations open to all the public, and the like. Each facility/source can be associated with an enterprise ID (associated with the photo) such that multiple facilities/sources can interact with the system 100. Public services associated with the enterprise ID can also be stored in association with the enterprise ID.

In addition or in lieu of accessing the public service URL, the system has capability to integrate with any health care provider/third party application that supports interoperability (e.g., CommonWell, HealtheIntent) to retrieve clinical documents to determine the required allergies, problems etc. Such sources may be EHR-agnostic interfaces to retrieve clinical documents from multiple HIE systems. Put simply, if a patient has visited Hospital A utilizing EHR system X on the east coast in the past and Hospital B (that utilizes EHR system Y, which is different from EHR system X) in the Midwest, and then Hospital C (that utilizes EHR system Z, different from both EHR system X and Y) on the west coast, the application can retrieve clinical documents from each of the different systems by interfacing with said sources. The information can be accessed from different HIE systems because of the interoperability with said sources. The above-mentioned health care provider(s)/third party application(s) can be integrated with (and, thus, provide access to the system described herein) any other clinical platform including information such as, for example, outpatient pharmacy medication lists, Consolidated Clinical Documents (CCDA), etc.

The facial recognition engine 106 can include an application that is continuously listening for receipt of images. Receipt of an image can trigger facial recognition analysis. The facial recognition engine 106 can be configured a variety of ways to perform facial recognition analysis. In embodiments, the facial recognition engine 106 indexes a face of an individual within a received reference image and stores the image. In embodiments, the facial recognition engine 106 generates a face identifier (also referred to herein as a FACE ID or a unique identifier), which is a mathematical or any other representation of the facial coordinates/face identified within the reference image. The FACE ID can be associated with the patient data associated with the reference image (e.g., the FACE ID, upon generation, can be associated with a patient identifier, a patient name, etc.) such that the FACE ID is used to identify the patient. Thus, once the FACE ID is generated, the reference image is no longer necessary. The reference image (along with the data associated therewith) can then be stored in any file/storage service/system (such as data store 110) along with the FACE ID. Alternatively, the FACE ID can be stored in a storage system (such as data store 110, for instance) in association with the patient metadata associated with the reference image, without storing the reference image itself. In further embodiments, the reference image can be stored in a storage system separate from the storage system in which the FACE ID and/or patient metadata is stored. The communication of the FACE ID, along with the patient metadata gleaned from the reference image, to a database is shown at instance 221.

To summarize the above, a reference image is received from a source and analyzed by facial recognition technology to identify a unique identifier (i.e., FACE ID) with which to associate the reference image. The reference image is associated with patient data, which is, in turn, associated with the unique identifier upon its generation. The unique identifier will be used throughout this disclosure to identify information about an unknown patient, as illustrated in the examples below.

As previously mentioned, there are at least thousands and thousands of instances of unidentified individuals being brought to emergency departments each year. An emergency responder could respond to a motor vehicle accident or a fire accident, for example, where the individuals involved are unresponsive. An individual may be found unresponsive with no identification in many situations. In the event where an unknown individual is encountered by a healthcare provider (e.g., emergency responder, etc.), the system 100 described herein may be utilized to identify the unidentified individual and receive health-related information associated therewith, among other things. In those instances, a source image can be acquired via a mobile device (e.g., a camera of a mobile device) associated with the healthcare provider. The mobile device can be identified as associated with the healthcare provider (e.g., authorized provider) to ensure only authorized devices can communicate with and receive information from the facial integration manager 112, for instance. Thus, a healthcare provider is not required to be associated with the mobile device but a mobile device is required to have been approved for communication with the facial integration manager 112. The source image comprises at least a portion of the unidentified individual's face.

A source device, such as source device 108, can acquire a source image and communicate the source image to the facial recognition engine 106, via the facial integration manager 112. In embodiments, the facial integration manager 112 is an application embodied on the source device 108. In embodiments, the facial integration manager 112 is embodied within the EHR server 104. In other aspects, the facial integration manager 112 is a decoupled service/application that is not tied to the EHR server 104 or the source device 108. The communication of a source photo to the facial recognition engine 106 is illustrated at instance 211.

The facial recognition engine 106, upon receipt of a source image, performs facial recognition analysis to identify a matching reference image or, more particularly, matching facial coordinates/data, or a lack thereof. In the event the facial coordinates of the source image do not match any facial coordinates (or a FACE ID) of a reference image, a notification indicating a match was not found can be communicated back to the facial integration manager 112 and, in turn, to the source device 108. When the facial recognition engine 106 determines that a FACE ID corresponds to the facial coordinates of the source image, the FACE ID, which is associated with patient information (from the reference image) is communicated to the facial integration manager 112 at instance 212. In embodiments, a confidence score is also communicated to the facial integration manager 112 along with the FACE ID. A confidence score, as used herein, refers generally to an indication of a likelihood that the facial coordinates of the source image are a match to the facial coordinates of the identified reference image. The confidence score can be represented as a percentage. Thresholds may be established such that a confidence score below a predetermined threshold is identified as an invalid match. A confidence score above a predetermined threshold may be considered a match.

The facial integration manager 112 can, utilizing the FACE ID, access demographic information for the patient associated with the FACE ID. In particular, the FACE ID may be stored in a data store (such as data store 110) with a mapping to a patient identifier (patient ID). The patient identifier can be used to access information about a patient such as a name, date of birth, residence information, and the like. The facial integration manager 112 can communicate the FACE ID to the data store 110 (or any storage component housing a FACE ID) at instance 213. The data store 110 can communicate the demographic data back to the facial integration manager 112 at instance 214. In embodiments, the data store 110 also communicates a patient identifier to the facial integration manager 112 along with the demographic information. The patient identifier, as explained herein, can be used to access additional information from a patient's EHR.

Once the facial integration manager 112 receives the demographic information, it immediately communicates the demographic information to the source device 108 at instance 216. The patient integration manger 112 continues on to identify relevant information for the now-identified patient. As shown at instance 217, the facial integration manager 112 communicates the patient identifier (received with the FACE ID demographic information) to a public URL via a service API call. Alternatively, the patient identifier could be used to access an EHR directly when a connection exists between the facial integration manager 112 and the EHR. Public URLs, in some embodiments, are associated with the EHR system. The URLs may be accessed to identify allergies of a patient, problems of a patient, diagnoses of a patient, and the like. Any information from an EHR could be accessed via the public URLs described herein if desired by the administrator. The facial integration manager 112 is programmed to request access to the information available at the public URL(s), at instance 217, and receive the available information at instance 218. The service URL/public URL can be protected such that only authorized requests are accepted. The facial integration manager 112 can filter out information that is not relevant or should not be communicated. In emergency situations, for example, an emergency responder does not have time to review an individual's entire medical history, nor is it necessary. Rather, an emergency responder needs to have relevant information provided quickly such as, but not limited to, allergies, problems, a history of violence or addiction, chronic medical conditions, and the like, if present. Of the information that is available to be provided to a source device, the facial integration manager 112 can rank the information such that information that is higher ranked is provided to the source device at instance 219. Thus, in embodiments, the facial integration manager 112 can receive all information available from the public URL for a patient and filter out unnecessary information (i.e., indicated as information to not communicate in an emergency situation) and rank the remaining information for a custom, prioritized communication of information. In other embodiments, the facial integration manager 112 can receive all information available from the public URL for a patient and rank all of the information to then filter out any information with a ranking below a predetermined threshold. The higher ranked/critical information (i.e., information not filtered out) can be communicated to the source device or can undergo another ranking (since the lower ranked/non-critical information was filtered out) and then be communicated to the source device based on the updated rankings. In aspects, allergies and problems are the highest ranked information from the EHR and will be selected, if present, to provide to the emergency responder (e.g., there can be situations where allergies or problems are not present and, thus, not communicated to a source device). In other aspects, the filtering steps described above may be performed by any other component and/or service the facial integration manager can call on to perform the steps. By way of example, and not limitation, a problem of Congestive Heart Failure (CHF) could be listed as a high priority (e.g., at the top of the list) while seasonal allergies could be not shown at all (i.e., filtered out as non-critical) or provided in the list since it is an allergy but shown toward the bottom of the list as it would rank lower in priority to a CHF condition. By way of further example, medications such as a blood thinner, beta blocker, or anti-seizure medication would be ranked higher than, for example, a stool softener or multivitamin. Any variations of highly ranked information can be provided to a source device (e.g., each type of information may not be present for each individual encountered and, thus, different information may be highly ranked for one person that may be ranked lower for another).

Furthermore, the ranking described herein can be performed by a variety of components of the system 100. For instance, the ranking may be performed by the facial integration manager 112 or by any of the public services described herein. The ranking could be performed with a rules engine (not shown) to evaluate specific parameters to compile the ranked list (e.g., the rules engine can be integrated with the facial integration manager 112, an EHR system, or be a stand-alone component). In other aspects, the ranking can be performed with integration with a clinical scoring or risk assessment scale (e.g., Glasgow Coma Scale for eye, verbal, and motor response problem ranking; VTE Venous Thromboembolism Risk Assessment).

The information provided above describes the interaction of various components of the system 100 to provide critical information to a source device where an unidentified individual is involved. Once the information is provided, the facial integration manager 112 continues on by dynamically, automatically generating at least a pre-arrival visit note and communicating the same to the source device at instance 222. A pre-arrival visit note, as used herein, refers generally to a note generated for a presenting individual prior to arrival at a destination. The pre-arrival visit note generally comprises demographic information (name, age, date of birth, sex, etc.) and a plurality of fields for additional information such as chief complaint, vital signs, allergies, problems, time to arrival at destination, estimated arrival time at destination, arrival method, medications given, etc. The pre-arrival visit form serves to place a patient on a tracking list, reserve a room for the patient, notify the clinicians of a patient status and any action already taken with respect to the patient, and the like. The pre-arrival visit form can also assist with providing prep time (i.e., time for preparation for the patient's arrival) at the ED facility to plan in the event of critical condition).

The facial integration manager 112 can utilize the demographic information received to pre-populate the pre-arrival visit note such that the emergency responder does not need to create the note or populate the demographic information. Additionally, the facial integration manager 112 can also pre-populate any other field of the pre-arrival note where information has been gathered (e.g., allergies, triage notes depicting the condition of the patient, etc.). The emergency responder can enter additional information into the pre-arrival visit note (e.g., speech to text). The first responder can dictate the condition of the patient and/or incident verbally and the application embodied on the mobile device can capture the audio and convert the audio to text and the same can be fed to the pre-arrival note. This will significantly improve the process efficiency and the patient care. Optionally the audio can be stored along with the text for any reference. After converting the speech to text, natural language processing (NLP)/artificial intelligent (AI) models may be utilized to train the model to return one or more recommendations. The pre-arrival visit note can also be communicated to the EHR server 104 at instance 220 to preserve the note in the patient's EHR. In addition to the pre-arrival visit note text, videos and/or images can be attached to the pre-arrival visit note. For example, it may be helpful to upload an image of an accident to indicate a severity of injuries For example, a crash impact is often helpful to administer proper care. In order to determine a crash impact and identify one or more recommendations automatically based on the picture, the system can leverage AI technologies and train the model to return the results such as a crash impact or one or more recommendations regarding care. By way of a specific example, a first responder can take a photo of an accident for crash impact analysis and, based on the damage to the vehicle, the application can generate a computational assessment of the injuries that a passenger(s) may have sustained, among other information derived from the image.

By way of another example, a first responder can speak (audio) and the audio can be converted to text that is run against an NLP/AI engine/model.

The model can also provide one or more recommendations based on information from the EHR and integration with one or more rules engines or risk assessment scales. For example, if the EHR provides "57 year old male, history of myocardial infarction," the model can ascertain that the patient likely has a history of surgery.

The model can also be trained to learn differences in audio inputs. For instance, if a user speaks with an accent, the model can be trained to identify the accent. Additionally, users can speak differently when under stress (e.g., may speak very fast or not clear). The model can be trained to identify speech even in those situations.

In embodiments, receipt of the pre-arrival visit note at the EHR (or the destination system, such as the ED) triggers a clinical workflow. In other words, the pre-arrival visit note is identified as received and a clinical workflow is initiated for the patient (before the patient arrived at the ED facility). Such a clinical workflow may include adding the patient to the tracking board, assigning a patient to a room, etc. Receipt of information, such as the pre-arrival visit note, in the EHR (or at the destination system) can also trigger notification of emergency contacts (accessed from the EHR server 104).

The application described herein provides interoperability between numerous systems to exchange private information and provide the information in necessary situations while still preserving the sensitive nature of the information.

Figure 3:
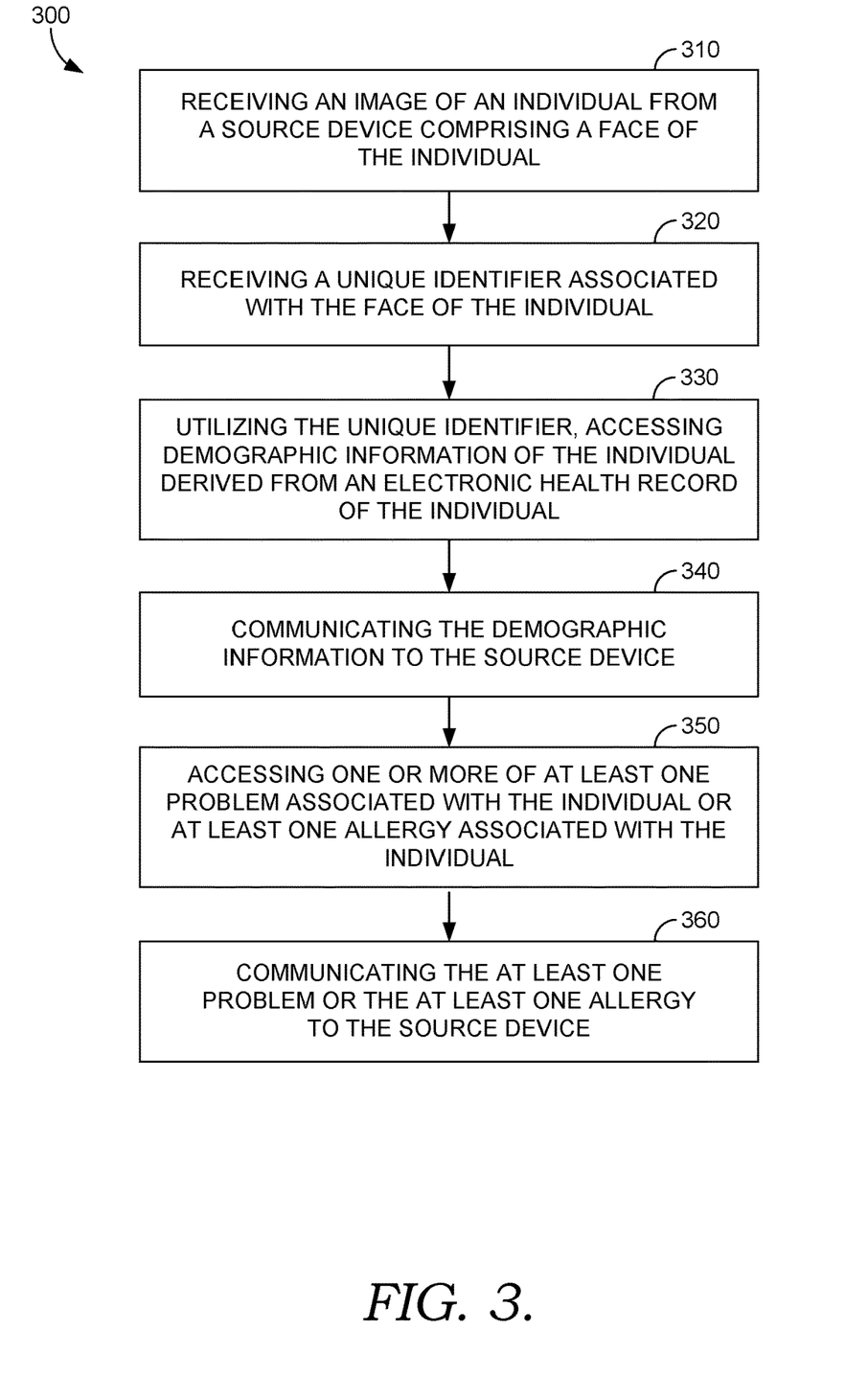
FIG. 3 is a flow diagram of an exemplary method in accordance with an embodiment of the present invention.

Turning now to FIG. 3, a flow diagram is provided showing a method 300 in accordance with some embodiments of the present invention. Initially, at block 310, an image of an individual is received from a source device. In embodiments, the image comprises a face of the individual or at least a portion thereof. In aspects, a plurality of source images can be uploaded. Additional images in cases where, for instance, there is a distortion of the patient's face, could help in obtaining a match in some cases. A unique identifier associated with the face of the individual is received at block 320. Utilizing the unique identifier, demographic information of the individual is accessed at block 330. The demographic information can be derived from an electronic health record of the individual. At block 340, the demographic information is communicated to the source device. At block 350, one or more of at least one problem associated with the individual or at least one allergy associated with the individual is accessed. At block 360, the at least one problem or the at least one allergy is communicated to the source device.

Figure 4:
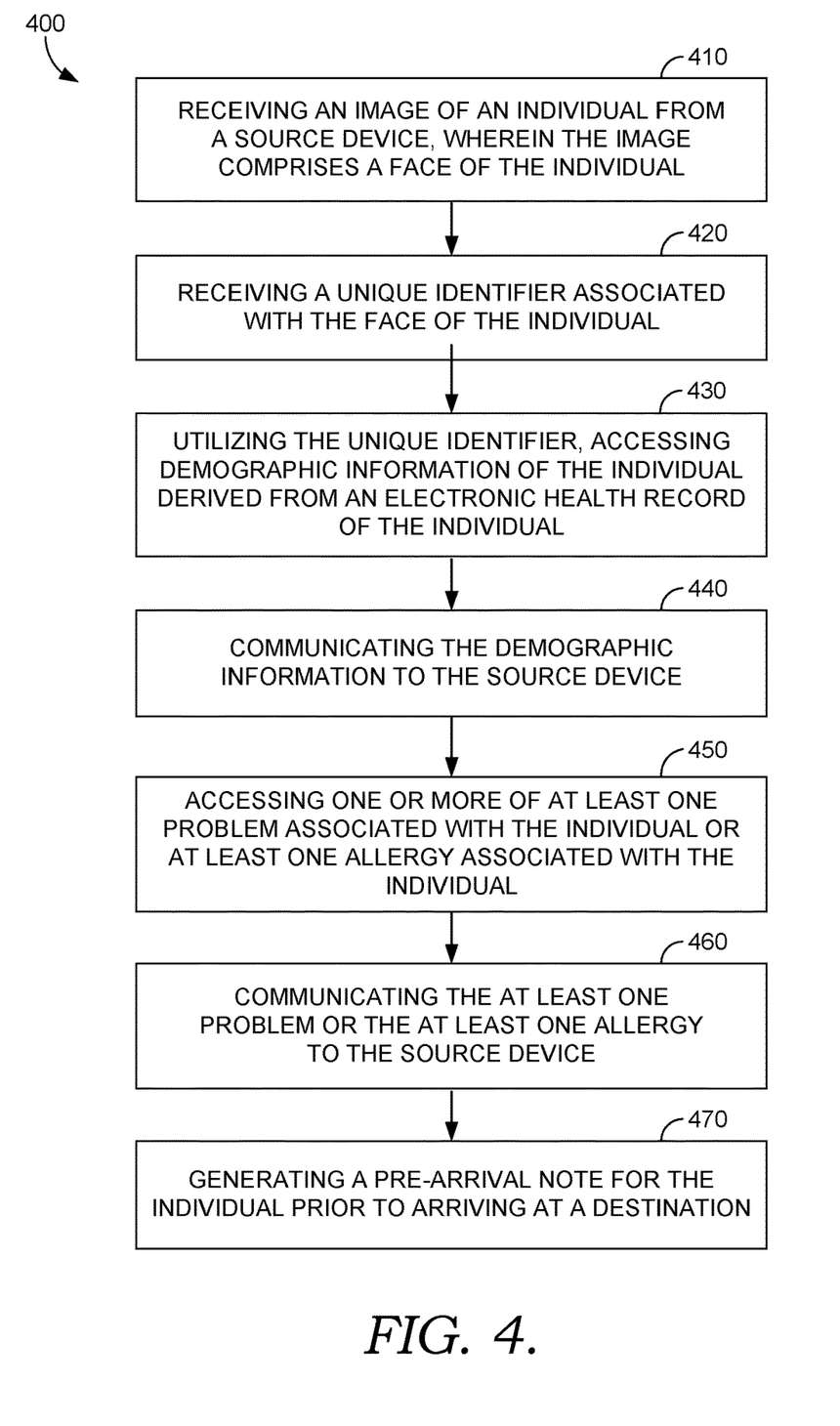
FIG. 4 is a flow diagram of an exemplary method in accordance with an embodiment of the present invention.

Turning now to FIG. 4, a flow diagram is provided showing a method 400 in accordance with some embodiments of the present invention. Initially, at block 410, an image of an individual is received from a source device, wherein the image comprises a face of the individual. A unique identifier associated with the face of the individual is received at block 420. Utilizing the unique identifier, demographic information of the individual is accessed at block 430, wherein the demographic information is derived from an electronic health record of the individual. At block 440, the demographic information is communicated to the source device. One or more of at least one problem associated with the individual or at least one allergy associated with the individual is accessed at block 450. The at least one problem or the at least one allergy is communicated to the source device at block 460. At block 470, a pre-arrival note (also referred to herein as a pre-arrival visit note) is generated for the individual prior to arriving at a destination, wherein the pre-arrival note is pre-populated with at least the demographic information.

Figure 5:
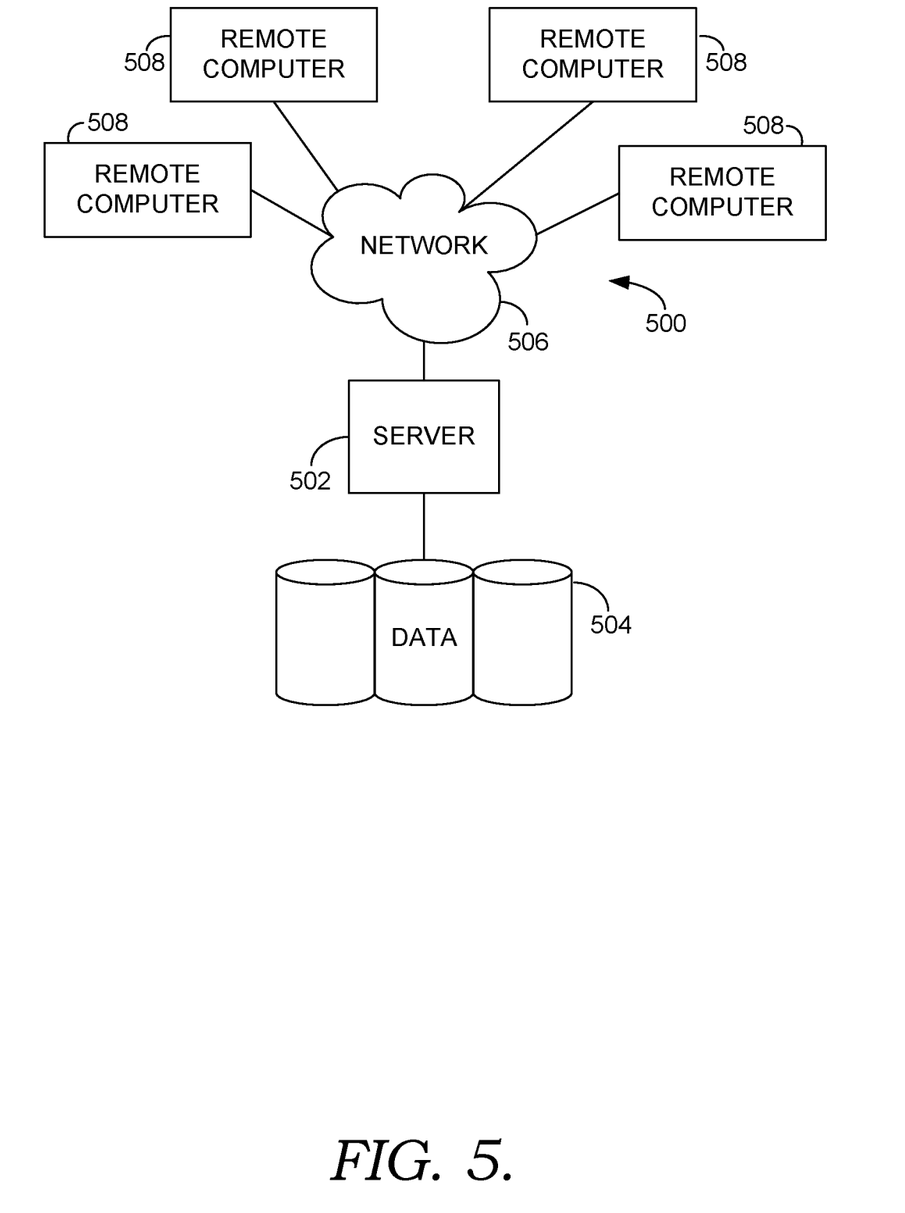
FIG. 5 depicts a block diagram of an exemplary computing environment suitable to implement embodiments of the present invention.

Turning to FIG. 5, it depicts a block diagram of an exemplary environment suitable to implement embodiments of the present invention. The exemplary computing environment 500 is suitable to implement embodiments of the present invention. It will be understood by those of ordinary skill in the art that the exemplary computing environment 500 is just one example of a suitable computing environment and is not intended to limit the scope of use or functionality of the present invention. Similarly, the exemplary computing environment 500 should not be interpreted as imputing any dependency and/or any requirements with regard to each component and combination(s) of components illustrated in FIG. 5. It will be appreciated by those having ordinary skill in the art that the connections illustrated in FIG. 5 are also exemplary as other methods, hardware, software, and devices for establishing a communications link between the components, devices, systems, and entities, as shown in FIG. 5, may be utilized in implementation of the present invention. Although the connections are depicted using one or more solid lines, it will be understood by those having ordinary skill in the art that the exemplary connections of FIG. 5 may be hardwired or wireless, and may use intermediary components that have been omitted or not included in FIG. 5 for simplicity's sake. As such, the absence of components from FIG. 5 should be not be interpreted as limiting the present invention to exclude additional components and combination(s) of components. Moreover, though devices and components are represented in FIG. 5 as singular devices and components, it will be appreciated that some embodiments may include a plurality of the devices and components such that FIG. 5 should not be considered as limiting the number of a devices or components.

Continuing, the exemplary computing environment 500 of FIG. 5 is illustrated as being a distributed environment where components and devices may be remote from one another and may perform separate tasks. The components and devices may communicate with one another and may be linked to each other using a network 506. The network 506 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 506, generally, provides the components and devices access to the Internet and web-based applications. The exemplary environment may also be a cloud computing environment.

The exemplary computing environment 500 comprises a computing device in the form of a server 502. Although illustrated as one component in FIG. 5, the present invention may utilize a plurality of local servers and/or remote servers in the exemplary computing environment 900. The server 502 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The server 502 may include or may have access to computer-readable media. Computer-readable media can be any available media that may be accessed by server 502, and includes volatile and nonvolatile media, as well as removable and non-removable media. By way of example, and not limitation, computer-readable media may include computer storage media and communication media. Computer storage media may include, without limitation, volatile and non-volatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 902. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the server 502 uses logical connections to communicate with one or more remote computers 508 within the exemplary computing environment 500. In one embodiment, the one or more remote computers 508 comprise external computer systems that leverage object-oriented programming. In embodiments where the network 506 includes a wireless network, the server 502 may employ a modem to establish communications with the Internet, the server 502 may connect to the Internet using Wi-Fi or wireless access points, or the server 502 may use a wireless network adapter to access the Internet. The server 502 engages in two-way communication with any or all of the components and devices illustrated in FIG. 5, using the network 506. Accordingly, the server 502 may send data to and receive data from the remote computers 508 over the network 506.

Although illustrated as a single device, the remote computers 508 may include multiple computing devices. In an embodiment having a distributed network, the remote computers 508 may be located at one or more different geographic locations. In an embodiment where the remote computers 508 are a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 508 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; students; and the like. In other embodiments, the remote computers 508 may be physically located in a non-medical setting, such as a packing and shipping facility or deployed within a fleet of delivery or courier vehicles. Remote computers 508 can also be hosted on a private or public cloud.

Continuing, the exemplary computing environment 500 includes a database 504. In some embodiments, the database 504 and at least the server 502, together, form a relational database management system. Although shown as a single component, the database 504 may be implemented using multiple data stores that are communicatively coupled to one another, independent of the geographic or physical location of a memory device. Exemplary data stores may also store data in the form of electronic records, for example, electronic medical records of patients, transaction records, billing records, task and workflow records, chronological event records, and the like. Database 504 can also be hosted on a private or public cloud.

Generally, the database 504 includes physical memory that is configured to store information encoded in data. For example, the database 504 may provide storage for computer-readable instructions, computer-executable instructions, data structures, data arrays, computer programs, applications, and other data that supports the functions and action to be undertaken using the exemplary computing environment 500 and components shown in exemplary FIG. 5.

In a computing environment having distributed components that are communicatively coupled via the network 506, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular data types. In embodiments, the server 502 may access, retrieve, communicate, receive, and update information stored in the database 504, including program modules. Accordingly, the server 502 may execute, using a processor, computer instructions stored in the database 504 in order to perform embodiments described herein.

Although internal components of the devices in FIG. 5, such as the server 502, are not illustrated, those of ordinary skill in the art will appreciate that internal components and their interconnection are present in the devices of FIG. 5. Accordingly, additional details concerning the internal construction of the device are not further disclosed herein.

The present invention has been described in relation to particular embodiments, which are intended in all respects to be illustrative rather than restrictive. Further, the present invention is not limited to these embodiments, but variations and modifications may be made without departing from the scope of the present invention.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations.

What is claimed is:

1. One or more non-transitory computer-readable media having executable instructions embodied thereon that, when executed by a processor of a computer device, perform a method, the method comprising:

receiving an image of an individual from a source device, wherein the image comprises a face of the individual;

receiving a unique identifier associated with the face of the individual, wherein the unique identifier includes a plurality of facial coordinates in the face of the individual in the image from the source device;

utilizing the unique identifier that includes the plurality of facial coordinates, identifying a patient identifier that has been mapped to the unique identifier;

accessing demographic information of the individual by utilizing the unique identifier that is mapped to the patient identifier, wherein the demographic information is derived from an electronic health record of the individual;

communicating the demographic information and a public URL that is associated with an Electronic Health Record (EHR) of the individual to the source device;

receiving a request to access the public URL from the source device;

based on the request from the source device, receiving authorization to access the public URL;

accessing, using the public URL that is associated with an Electronic Health Record (EHR) of the individual, at least one of a problem or an allergy that is stored in the EHR associated with the individual; and communicating the at least one of the problem or the allergy to the source device.

2. The media of claim 1, wherein the image is captured by a camera of the source device.

3. The media of claim 1, wherein the source device is associated with an emergency responder.

4. The media of claim 1, wherein the method further comprises:

receiving a confidence score indicating a likelihood of a match of a reference image to the image.

5. The media of claim 4, wherein the confidence score is a percentage indicator.

6. The media of claim 1, wherein the method further comprises uploading one or more additional images to the electronic health record of the individual.

7. One or more non-transitory computer-readable media having executable instructions embodied thereon that, when executed by a processor of a computer device, perform a method, the method comprising:

receiving an image of an individual from a source device, wherein the image comprises a face of the individual;

receiving a unique identifier associated with the face of the individual wherein the unique identifier includes a plurality of facial coordinates in the face of the individual in the image from the source device;

utilizing the unique identifier that includes the plurality of facial coordinates, identifying a patient identifier that has been mapped to the unique identifier;

accessing demographic information of the individual by utilizing the unique identifier that is mapped to the patient identifier, wherein the demographic information is derived from an electronic health record of the individual;

communicating the demographic information and a public URL that is associated with an Electronic Health Record (EHR) of the individual to the source device;

receiving a request to access to the public URL from the source device;

based on the request from the source device, receiving authorization to access the public URL;

accessing, using the public URL that is associated with an Electronic Health Record (EHR) of the individual, at least one of a problem associated with the individual or an allergy associated with the individual that is stored in the EHR;

communicating the at least one of the problem or the allergy to the source device; and generating a pre-arrival note for the individual prior to arriving at a destination, wherein the pre-arrival note is pre-populated with at least the demographic information.

8. The media of claim 7, wherein the destination is a healthcare facility.

9. The media of claim 8, wherein the healthcare facility is an emergency department.

10. The media of claim 7, wherein the image is captured by a camera of the source device.

11. The media of claim 10, wherein the source device is associated with an authorized emergency responder.

12. The media of claim 7, wherein the method further comprises:
uploading one or more additional images to the electronic health record of the individual.

13. The media of claim 7, wherein the method further comprises receiving a confidence score indicating a likelihood of a match of a reference image to the image.

14. The media of claim 10, wherein the unique identifier is received from a facial recognition engine that previously generated the unique identifier from a reference image, wherein the unique identifier is a mathematical representation of facial coordinates obtained from a reference image of the individual.

15. A system for clinical integration of facial recognition, the system comprising:
one or more processors configured to:
receive an image of an individual from a source device, wherein the image comprises a face of the individual;
receive a unique identifier associated with the face of the individual, wherein the unique identifier by utilizing the unique identifier that is mapped to the patient identifier facial coordinates in the face of the individual in the image from the source device;
utilize the unique identifier that includes the plurality of facial coordinates to identify a patient identifier that has been mapped to the unique identifier;
access demographic information of the individual by utilizing the unique identifier that is mapped to the patient identifier, wherein the demographic information is derived from an electronic health record of the individual;
communicate the demographic information and a public URL that is associated with an Electronic Health Record (EHR) of the individual to the source device;
receive a request to access to the public URL from the source device;
based on the request from the source device, receiving authorization to access the public URL;
access, using the public URL that is associated with an Electronic Health Record (EHR) of the individual, at least one of a problem or an allergy that is stored in the EHR associated with the individual; and
communicate the at least one of the problem or the allergy to the source device.

16. The system of claim 15, wherein the image is captured by a camera of the source device, and wherein the source device is associated with an emergency responder.

17. The system of claim 15, wherein the one or more processors are further configured for generating a pre-arrival note for the individual prior to arriving at a destination, wherein the pre-arrival note is pre-populated with at least the demographic information.

18. The system of claim 17, wherein the pre-arrival note is further pre-populated with the at least one or the problem or allergy associated with the individual and triage notes.

* * * * *